United States Patent
Olsen et al.

(10) Patent No.: US 8,702,724 B2
(45) Date of Patent: Apr. 22, 2014

(54) THROMBUS RETRIEVAL DEVICE

(75) Inventors: Kian Olsen, Vallensbaek Strand (DK); Carsten Skødt, Sorø (DK); Anders Ginge Jensen, Ringsted (DK); Frank Christiansen, Haslev (DK); Per Elgård, Haslev (DK)

(73) Assignee: Cook Medical Technologies LLC, Bloomington, IN (US)

( * ) Notice: Subject to any disclaimer, the term of this patent is extended or adjusted under 35 U.S.C. 154(b) by 182 days.

(21) Appl. No.: 12/643,204

(22) Filed: Dec. 21, 2009

(65) Prior Publication Data
US 2010/0292726 A1    Nov. 18, 2010

(30) Foreign Application Priority Data

May 18, 2009  (GB) .................................. 0908500.2

(51) Int. Cl.
*A61B 17/22* (2006.01)
(52) U.S. Cl.
USPC ....................................................... 606/127
(58) Field of Classification Search
USPC ......... 606/200, 191, 198, 159, 194, 108, 213, 606/128, 127, 46, 47, 170, 171, 167, 606/110–115, 48, 45; 623/1.11; 604/104–109, 262, 267; 600/562–572, 600/206, 106, 184, 104, 107, 114, 373, 374, 600/385, 393; 607/113, 125–128, 122
See application file for complete search history.

(56) References Cited

U.S. PATENT DOCUMENTS

| | | | |
|---|---|---|---|
| 4,485,812 A * | 12/1984 | Harada et al. | 606/47 |
| 5,683,384 A * | 11/1997 | Gough et al. | 606/41 |
| 5,752,961 A * | 5/1998 | Hill | 606/113 |
| 5,964,727 A | 10/1999 | Edwards et al. | |
| 6,193,672 B1 * | 2/2001 | Clement | 600/565 |
| 6,280,441 B1 * | 8/2001 | Ryan | 606/45 |
| 6,287,304 B1 * | 9/2001 | Eggers et al. | 606/37 |
| 6,302,870 B1 * | 10/2001 | Jacobsen et al. | 604/272 |
| 6,402,744 B2 * | 6/2002 | Edwards et al. | 606/41 |
| 6,517,550 B1 * | 2/2003 | Konya et al. | 606/113 |
| 6,540,695 B1 * | 4/2003 | Burbank et al. | 600/564 |
| 6,607,520 B2 * | 8/2003 | Keane | 606/2 |
| 6,638,276 B2 * | 10/2003 | Sharkey et al. | 606/41 |
| 7,101,378 B2 * | 9/2006 | Salameh et al. | 606/113 |
| 7,322,939 B2 * | 1/2008 | Burbank et al. | 600/564 |
| 2001/0012934 A1 * | 8/2001 | Chandrasekaran et al. | 606/41 |
| 2001/0051783 A1 * | 12/2001 | Edwards et al. | 604/22 |
| 2003/0018346 A1 * | 1/2003 | Follmer et al. | 606/159 |
| 2004/0153004 A1 * | 8/2004 | Burbank et al. | 600/567 |
| 2004/0220604 A1 | 11/2004 | Fogarty et al. | |
| 2005/0119668 A1 | 6/2005 | Teague et al. | |
| 2006/0149295 A1 * | 7/2006 | Fleming, III | 606/113 |

(Continued)

FOREIGN PATENT DOCUMENTS

EP      0765138 B1    9/1998
WO    WO 95/35066   12/1995

(Continued)

*Primary Examiner* — Kathleen Holwerda
*Assistant Examiner* — Jocelin Tanner
(74) *Attorney, Agent, or Firm* — Brinks Gilson & Lione

(57) ABSTRACT

A thrombus retrieval device has one or more thrombus engaging elements that are movable between a retracted configuration in which they are stowed within the device and a deployed configuration in which they project from the device to snare an adjacent thrombus for removal from a blood vessel.

16 Claims, 6 Drawing Sheets

(56) References Cited

U.S. PATENT DOCUMENTS

| | | |
|---|---|---|
| 2007/0185511 A1* | 8/2007 | Minosawa et al. ............ 606/170 |
| 2007/0265648 A1 | 11/2007 | Cohen |
| 2008/0051756 A1* | 2/2008 | Makower et al. ............. 604/508 |
| 2008/0208075 A1 | 8/2008 | Goldenberg |
| 2008/0221604 A1 | 9/2008 | Kondoh et al. |

FOREIGN PATENT DOCUMENTS

| | | |
|---|---|---|
| WO | WO 99/44506 | 9/1999 |
| WO | WO 02/055146 | 7/2002 |
| WO | WO 02055146 A1 | 7/2002 |
| WO | WO 2004/069290 | 8/2004 |
| WO | PCT20090069069 | 4/2010 |

\* cited by examiner

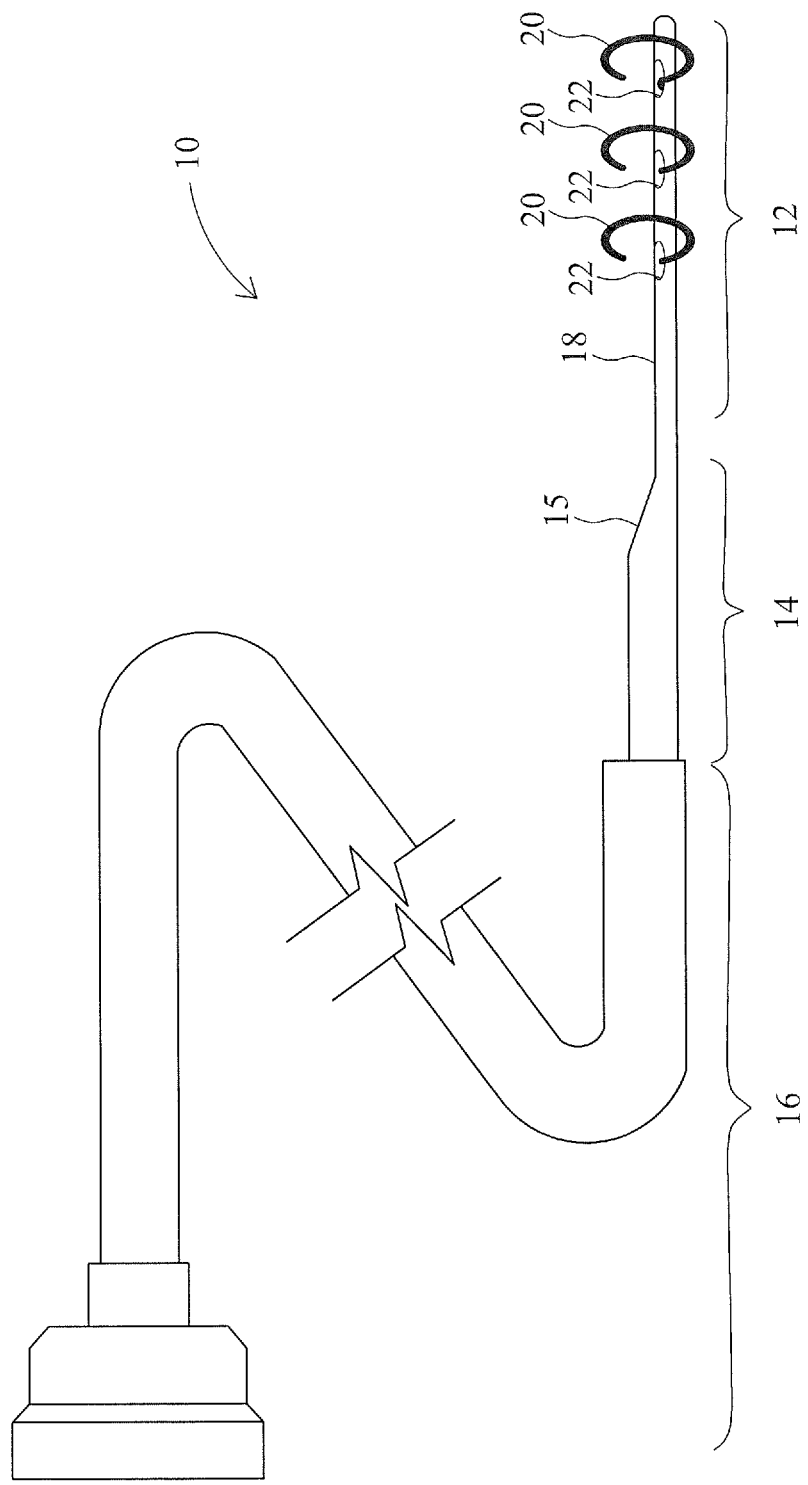

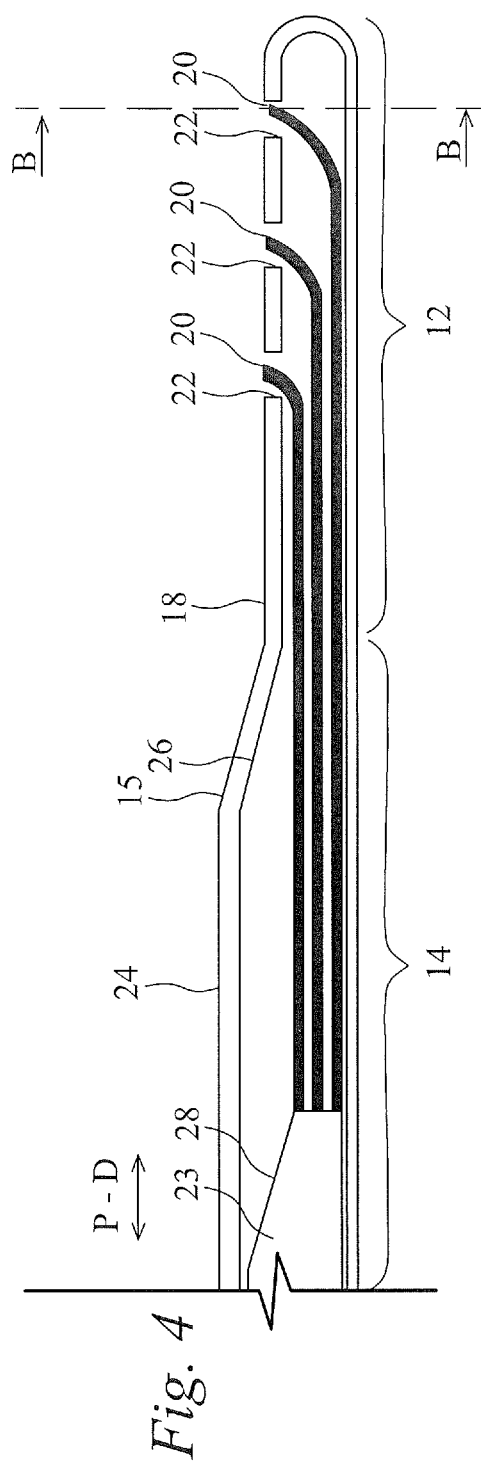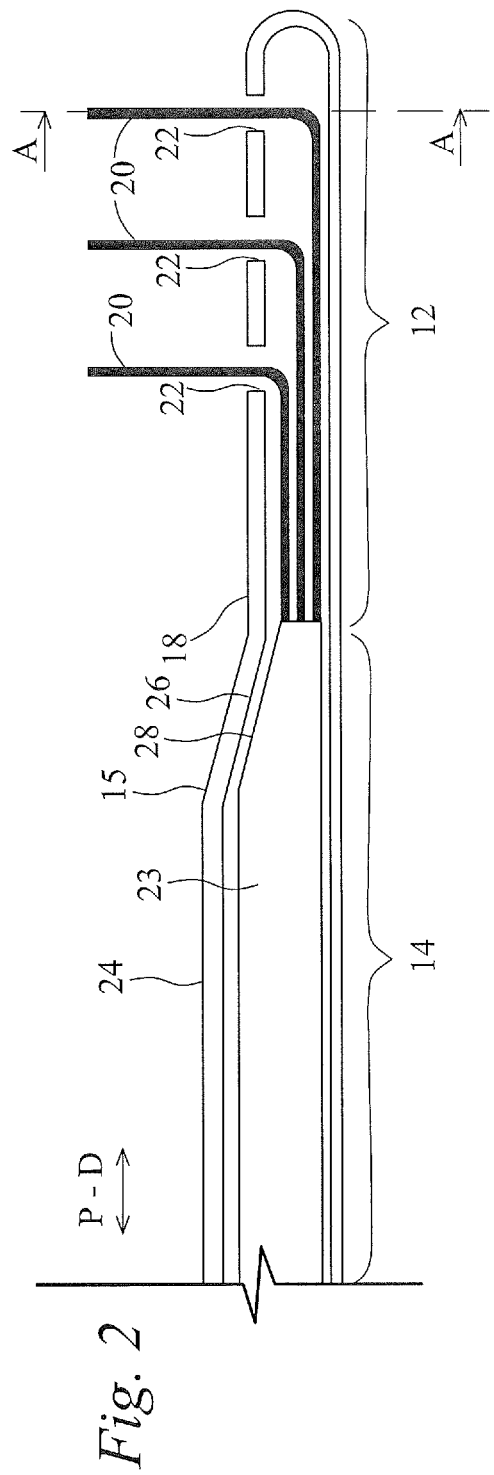

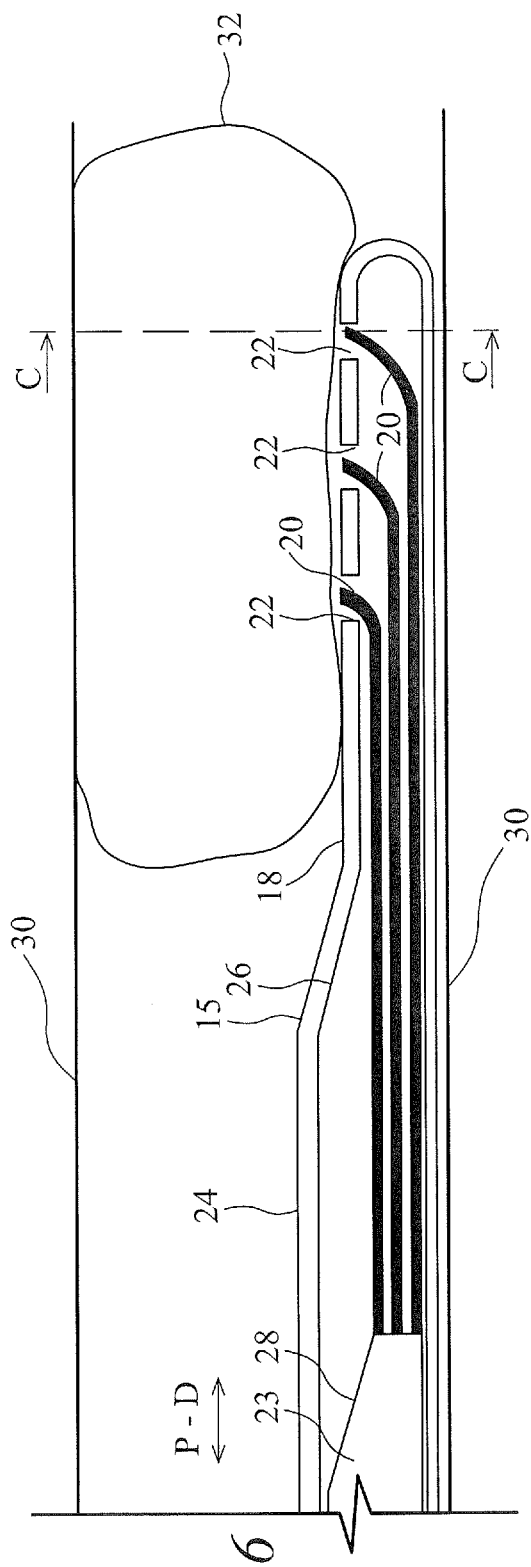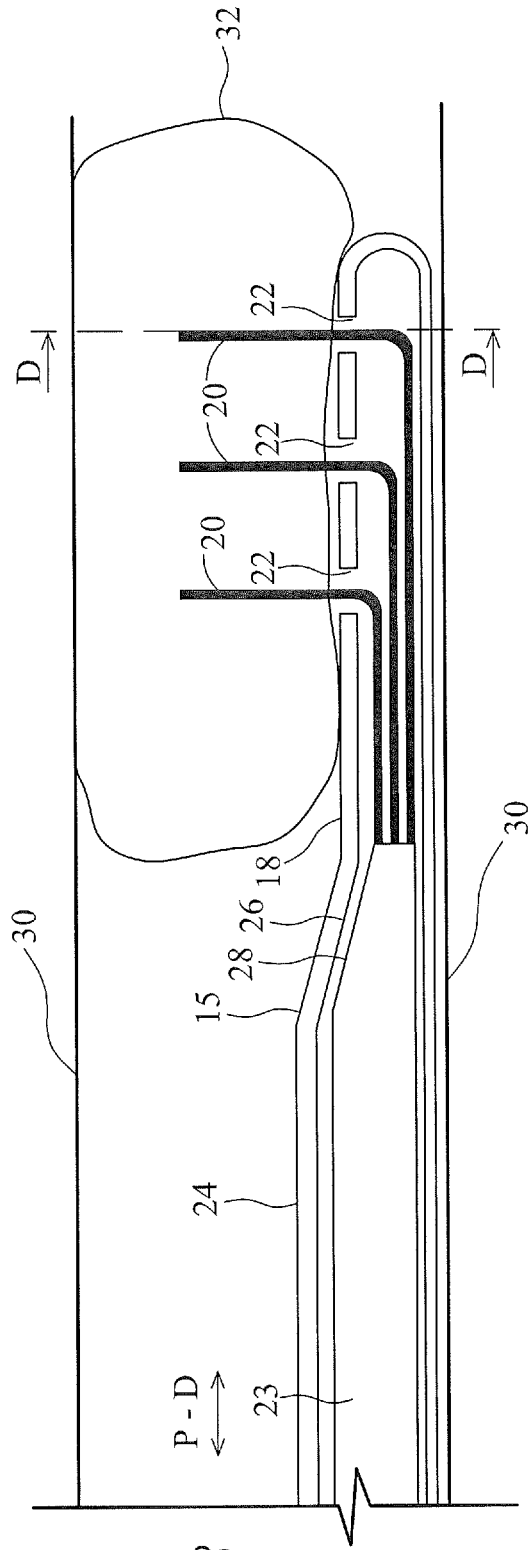

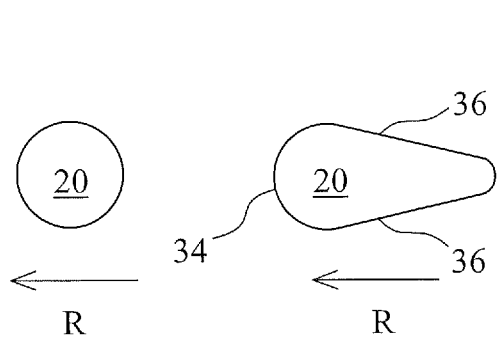
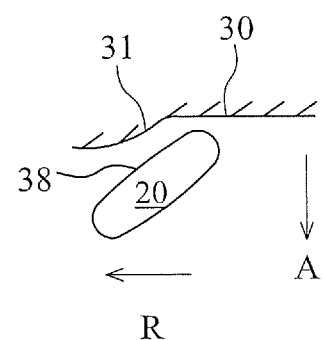
Fig. 10    Fig. 11    Fig. 12
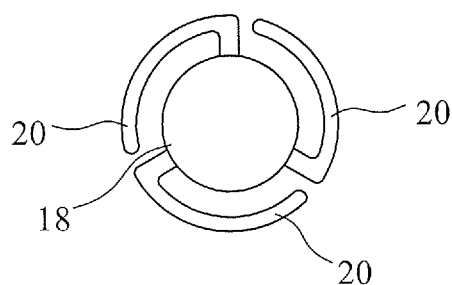
Fig. 13
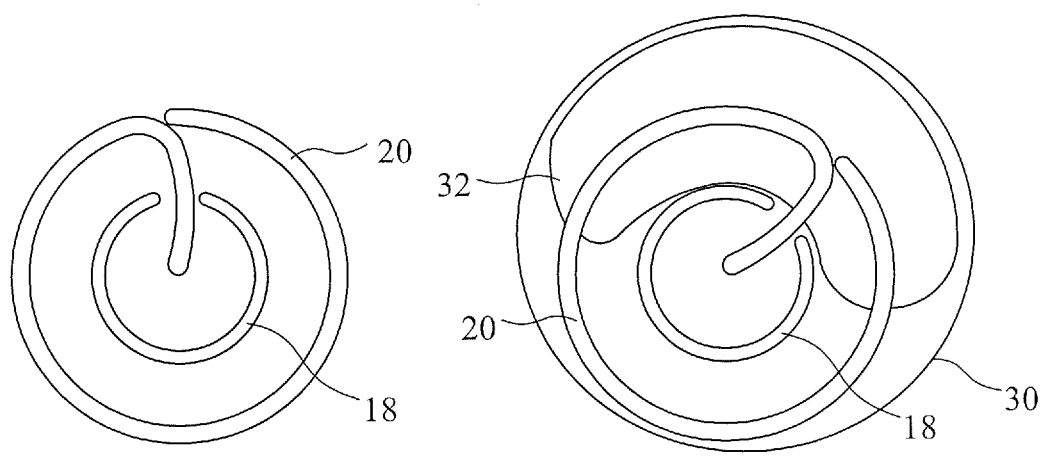
Fig. 14    Fig. 15

THROMBUS RETRIEVAL DEVICE

CROSS-REFERENCE TO RELATED APPLICATIONS

This application claims priority of UK Patent Application No. 0908500.2, filed May 18, 2009.

TECHNICAL FIELD

The present invention relates to a snare for the retrieval of occluding bodies from lumen. The invention has particular, although not exclusive relevance to the in-vivo retrieval of intracranial soft thrombi.

BACKGROUND OF THE INVENTION

Ischeamic cerebrovascual accidents can be caused by full or partial occlusion of the brain's arterial blood vessels, for example by intracranial thrombi or emboli, or by thrombi in the dural venous sinuses that drain blood from the brain.

The removal of occluding bodies from the cerebral vasculature may be achieved by pharmacological means, for example by thrombolysis, or by mechanical means, for example by physically breaking a thrombus or embolus into a number of pieces prior to its removal.

The breaking into pieces of an occluding body can be deleterious as dislodged parts may travel through the cerebral vasculature and subsequently form emboli themselves. Blocking and/or suction means are therefore required to ensure that dislodged parts are safely collected. The need for blocking and/or suction means limits the size of vessels in which such an approach can be employed and precludes its application for many of the small and tortuous intracranial blood vessels, for example the branch vessels of the circle of Willis or middle cerebral artery, and arteries arising from the distal vertebral and basilar arteries.

SUMMARY OF THE INVENTION

According to one aspect, the present invention provides a device for the retrieval of a thrombus from a vessel, the device comprising: a delivery tube with at least one side hole oriented radially; and one or more thrombus engaging elements for each side hole, each thrombus engaging element comprising a wire and being movable radially of the delivery tube between a retracted configuration in which it is retained within the delivery tube and a deployed configuration in which it projects from the delivery tube through the side hole.

These and various other aspects of the invention will become apparent from the following detailed description which is given by way of example only and which is described with reference to the accompanying Figures in which:

BRIEF DESCRIPTION OF THE DRAWING

FIG. 1 shows a perspective view of catheter having a thrombus retrieval device arranged in a deployed configuration;

FIG. 2 shows a longitudinal cross-section of the retrieval device of FIG. 1 in the deployed configuration;

FIG. 4 shows a longitudinal cross-section of the retrieval device of FIG. 1 arranged in a retracted configuration;

FIG. 6 shows a longitudinal cross-section of the retrieval device of FIG. 1 arranged in the retracted configuration and positioned in a blood vessel adjacent to a thrombus;

FIG. 8 shows a longitudinal cross-section of the retrieval device of FIG. 1 arranged in the deployed configuration and positioned in a blood vessel adjacent to a thrombus;

FIGS. 10, 11, and 12 show cross-sectional profiles of example curly wires of the retrieval device;

FIG. 13 shows an end view of the retrieval section of an alternative embodiment;

FIG. 14 shows an end view of the retrieval section of an alternative embodiment;

FIG. 15 shows a transverse cross-section of the retrieval device of FIG. 14 arranged in the deployed configuration and positioned in a blood vessel adjacent to a thrombus.

DETAILED DESCRIPTION

Figure 5:
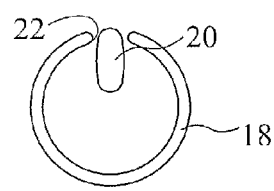
FIG. 5 shows a transverse cross-section of the retrieval device of FIG. 4.

FIG. 1 shows a perspective view of a flexible catheter 10 having a thrombus retrieval section 12, a pushing section 14, and a delivery and removal section 16. The retrieval section 12 comprises a flexible delivery tube 18 of small diameter, and three thrombus engaging elements, in this case curly wires 20, made of an elastic material and having a predetermined shape. In FIG. 1 the curly wires 20 are shown in a deployed configuration in which their distal ends project radially from respective holes 22 of the flexible delivery tube 18. In this configuration, the distal ends are unconstrained and so take their undeformed shapes which correspond to approximate semicircles in the radial plane. The pushing section 14 is flexible and is fixedly coupled to, and has a larger diameter than, the retrieving section 12. The delivery and removal section 16 is a flexible tube having an internal diameter that is large enough for both the pushing section 14 and the retrieval section 12 to be retracted therethrough when the retrieval section 12 is in the deployed configuration and is ensnaring a thrombus.

FIG. 2 shows a longitudinal cross-section of the flexible catheter 10 of FIG. 1 when in the deployed configuration. The proximal ends of the curly wires 20 are retained within the flexible delivery tube 18 and are fixedly coupled, for example by welding, soldering, or gluing, to a pushing member 23. The pushing member 23 is slidable within an outer tube 24 of the pushing section 14 in a proximal-distal direction (as indicated by arrow P-D of FIG. 2) and has a larger cross-sectional area than the curly wires 20 so as to facilitate the transmission of a pushing force from a surgeon, or another operator of the flexible catheter 10, to the curly wires 20. The outer tube 24 of the pushing section 14 has a stop surface 26 arranged to abut with a corresponding stop surface 28 of the pushing member 23 to prevent the pushing member 23 pushing the curly wires 20 out of the holes 22 by more than a predetermined amount.

Figure 3:
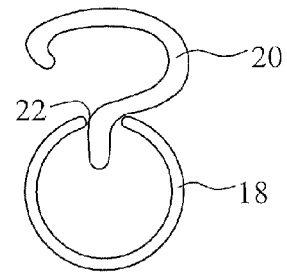
FIG. 3 shows a transverse cross-section of the retrieval device of FIG. 2.

FIG. 3 shows a transverse cross-section along line A-A of FIG. 2 of the retrieval section 12 in the deployed configuration. The distal end of a curly wire 20 can be seen projecting from a hole 22 in the flexible delivery tube 18. As the distal end of the curly wire 20 is unconstrained by the flexible delivery tube 18, it is in its undeformed shape which in this case corresponds to a semicircle-like loop in the transverse (or radial) plane of the flexible delivery tube 18.

FIG. 4 shows a longitudinal cross-section of the flexible catheter 10 in a retracted configuration. In the retracted configuration, the pushing member 23 is less advanced in the distal direction with respect to the outer tube 24 of the pushing section 14 than in the deployed configuration and the distal ends of the curly wires 20 are entirely contained within the flexible delivery tube 18; FIG. 5, which shows a transverse cross-section along line B-B of FIG. 4 of the retrieval section 12, illustrates this further. In this configuration, the curly wires 20 have been elastically deformed from their undeformed, curly, state and, due to flexible delivery tube 18, are constrained to be relatively straight.

In operation, prior to insertion into a patient's body, the pushing member 23 of the flexible catheter 10 is set up so that the distal ends of the curly wires 20 are adjacent their respective holes 22, but do not project therefrom. Pushing member 23 is then locked with respect to the outer tube 24 of the pushing section 14 in the retracted configuration by a locking mechanism (not shown) to prevent unintended deployment of the curly wires 20 during delivery of the retrieval section 12 to the site of the thrombus.

To access the intracranial vessel from which a thrombus is to be removed, a percutaneous incision is made in the patient, for example to access the carotid, subclavian, or femoral artery. The flexible catheter 10 in the retracted configuration is then introduced via the incision into the patient's arterial system and advanced to the site of the thrombus in a two-stage procedure under the guidance of an imaging system, for example X-ray, ultrasound, magnetic resonance imaging, or any combination thereof. Contrast enhancement agents may be employed in order to facilitate identification of the location of the thrombus. In the first stage of catheter advancement, the delivery and removal section 16, which has a larger cross-sectional profile than those of the pushing and retrieval sections 14, 12, is advanced towards the site of the thrombus until the blood vessels through which it is being advanced narrow to prevent further advancement—typically this occurs 10-15 cm away from the thrombus. In the second stage of catheter advancement, the pushing and retrieval sections 14, 12 are advanced with respect to the delivery and removal section 16 until the tip of the flexible delivery tube 18 of the retrieval section 12 is next (or proximally adjacent) to the thrombus.

Figure 7:
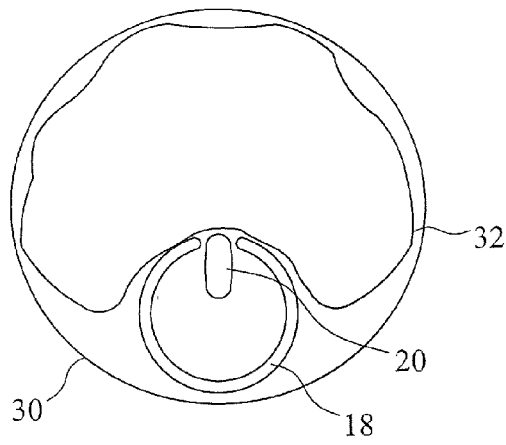
FIG. 7 shows a transverse cross-section of the retrieval device of FIG. 6.

Once the tip of the flexible delivery tube 18 of the retrieval section 12 is next to the thrombus, the flexible catheter 10 is further advanced so that the retrieval section 12 lies to one side of (or is radially adjacent to) the thrombus and the holes 22 face (or open in the direction of) the thrombus. If the thrombus totally occludes the blood vessel then the retrieval section 12 is advanced through the thrombus to reach such a position. As the flexible catheter 10 is in the retracted configuration, it has a small cross-sectional profile and can therefore easily be advanced to such a position. FIG. 6 shows the flexible delivery tube 18 inside a blood vessel 30 having a thrombus 32. As can be seen, the retrieval section 12 lies to one side of the thrombus 32 and the holes 22 face the thrombus 32. FIG. 7 shows a cross-sectional view along line C-C of FIG. 6 and further illustrates how the flexible delivery tube 18 lies to one side of the thrombus.

Once the retrieval section 12 is located to one side of the thrombus 32 and the holes 22 face the thrombus 32, the locking mechanism (not shown) that prevents movement of the pushing member 23 with respect to the outer tube 24 of the pushing section 14 is released and the pushing member 22 is advanced in the distal direction until the stop surface 28 of the pushing member 23 contacts the stop surface 26 of the outer tube 24 of the pushing section 14. This pushes the distal ends of the curly wires through their respective holes 22. As the curly wires 20 pass through the holes 22, they spring back into their undeformed shapes and advance into the thrombus 32 thereby ensnaring it. As only the distal tips of the curly wires 20 pierce the thrombus 32, the amount of force required to push the curly wires into the thrombus 32 is relatively small. By only making small punctures in the thrombus 32, the chance of the thrombus breaking up is significantly reduced.

Figure 9:
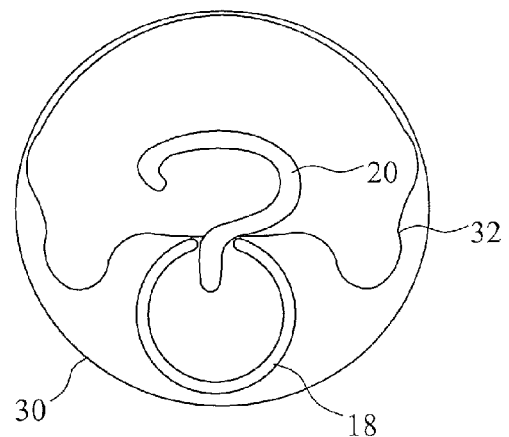
FIG. 9 shows a transverse cross-section of the retrieval device of FIG. 8.
Figure 16:
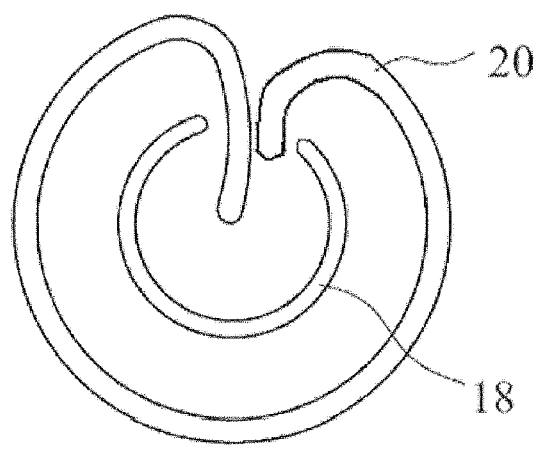
FIG. 16 shows an end view of the retrieval section of a further alternative embodiment.

Like FIG. 6, FIG. 8 shows the flexible delivery tube 18 inside the blood vessel 30 and to one side of the thrombus 32; however, in FIG. 8 the curly wires 20 are shown in the deployed configuration having advanced into the thrombus 32. FIG. 9 shows a cross-sectional view along line D-D of FIG. 8 and further illustrates how the curly wires 20 have advanced into the thrombus 32.

Once the curly wires 20 have been deployed into the thrombus 32, the locking mechanism (not shown) that prevents movement of the pushing member 23 with respect to the outer tube 24 of the pushing section 14 is locked to prevent the curly wires 20 from retracting from the thrombus 32 during removal of the flexible catheter 10. The ensnared thrombus is then removed from the vessel 30 by retracting the retrieval and pushing sections 12, 14 into the delivery and removal section 16. Once the retrieval section 12 and the thrombus 32 that it ensnares are retracted into the delivery and removal section 16, the risk of parts of the ensnared thrombus breaking off during retraction of the flexible catheter 10 from the vascular system is reduced and the flexible catheter 10 is withdrawn from the patient.

By removing the thrombus as a whole instead of breaking it into a number of pieces for individual removal, the risk of pieces escaping and subsequently forming emboli is reduced. Also, as sucking or blocking means for capturing all of the removed pieces are not required, the above described apparatus has a small cross-sectional area and may be used for vessels having a smaller diameter than would be possible for techniques that break thrombi into a number of pieces.

A person skilled in the art will appreciate that, although the above describes the removal of a thrombus from the arterial cerebral vasculature, the apparatus could equally be employed to remove emboli and/or be used in the venous cerebral vasculature. As another possibility, the apparatus could be employed for the removal of thrombi or emboli from other parts of the body, for example from the coronary or pulmonary arteries and/or the branch vessels thereof.

In the embodiment of FIGS. 1 to 9, the pushing section 14 has a larger diameter than the retrieving section 12; as another possibility, the pushing section may have a diameter about the same as the diameter of the retrieving section 12 thereby increasing the range of thrombi that the retrieving section 12 can reach. In such an embodiment, the tapered shoulder 15 of the retrieving section 12 would not be present.

In addition to the stop surfaces 26, 28 that constrain the motion of the pushing member 23 in the distal direction, the motion of the pushing member 23 in the proximal direction may also be constrained by a pair of complimentary stopping surfaces (not shown) arranged to prevent the curly wires 20 from being retracted with respect to the holes 22 by more than a predetermined amount—thereby ensuring that the curly wires 20 do not lose alignment with their respective holes 22.

The pushing member 23 may be keyed to the outer tube 24 of the pushing section 14 to prevent twisting of the outer tube 24 from causing misalignment between the curly wires 20 and their respective holes 22 as could occur during advancement of the flexible catheter 10 to the thrombus. By making the pushing member 23 subject to the same twisting as the outer tube 24, changes in the projection/retraction of the curly wires 20 from their respective holes 22 due to bending of the flexible catheter 10 are minimised, thereby keeping the profile of the flexible delivery tube 18 low whilst the catheter is in the retracted configuration, and preventing movement of the curly wires 20 with respect to an ensnared thrombus when the flexible catheter 10 is removing the thrombus.

The flexible delivery tube 18 may further comprise one or more guide portions (not shown) arranged to guide the curly wires to their respective holes 22. Such guide portions may comprise one or more wire-specific tubes within which each curly wire 20 slides, or may comprise one or more internal baffles to direct the passage of the curly wires 20. The presence of guide portions may allow the curly wires 20 to be withdrawn more than would otherwise be possible without them becoming misaligned from their respective holes 22, and may facilitate assembly of the flexible catheter 10.

To enhance the transmission of force from the pushing member 23 to the curly wires 20, adjacent proximal portions of the curly wires 20 that do not project from the holes 22 when the flexible catheter 10 is in the deployed configuration, may be bonded to one another. As another possibility, the curly wires 20 may form a single component with only the distal tips of the wires projecting from a main body thereof.

Instead of having a semicircle-like shape, the curly wires 20 may have a shape such that, upon deployment, they curl back on themselves so that their distal ends enter into one or more holes in the flexible delivery tube 18 leaving only intermediate portions of the curly wires outside of the flexible delivery tube 18. By having the ends of the curly wires 20 stowed inside the flexible delivery tube 18, the possibility of any of these ends digging into a vessel wall upon retraction of the flexible catheter 10 is removed.

The outer diameter of the flexible delivery tube 18 is preferably in the range 3Fr to 2Fr (where the diameter in millimeters is determined by dividing the Fr size by 3), and more preferably 2.2Fr. By having a small cross-section, the chances of breaking thrombi into pieces during positioning of the flexible delivery tube 18 is reduced. The outer diameters of the curly wires 20 need to be such that they are able to fit within the flexible delivery tube 18; they may, for example, be as small as 0.06 mm.

The more curly wires 20 that the flexible catheter 10 has, the better it will be able to ensnare thrombi; however, as the number of curly wires 20 increases, so too will the cross-sectional size of the flexible delivery tube 18. The flexible catheter 10 preferably has between three and five curly wires 20, and more preferably three.

The curly wires 20 may have cross-sectional profiles that are circular, or they may have one or more flattened portions to increase the surface area of the curly wires that is available for engagement with thrombi. The cross-sectional profiles of the curly wires 20 may be shaped and/or oriented so as to reduce the risk of the curly wires 20 digging into vessel walls during deployment and/or retraction, for example, the cross-sectional profile may be chosen so as to not comprise any corners or highly curved portions. FIGS. 10, 11, and 12 show example cross-sectional profiles of the curly wires 20 and indicate with arrow 'R' the direction in which the curly wire 20 will be pulled when the retrieval section 12 is retracted into the delivery and removal section 16. As the profile of FIG. 10 is circular, it presents no sharp edges or barbs with which to dig into blood vessels during retraction. The leading edge of the profile of FIG. 11 is a semicircle 34 of large diameter and so, like the profile of FIG. 1, will not present surrounding blood vessel walls with sharp edges during retraction. The profile of FIG. 11 also comprises a pair of flat edges 36 for increasing the surface area of the curly wire 20 that is available for gripping with thrombi. The profile of FIG. 12 is shown next to a portion of vessel wall 30, and is oriented with respect to the vessel wall 30 such that, upon retraction in direction R, if the curly wire 20 encounters a protrusion 31 or change in direction of the vessel wall 30, the edge 38 of the curly wire 20 acts to push the curly wire 20 in direction A away from the protrusion 31 wall thereby reducing the risk of the curly wire digging into the vessel wall 30 or the protrusion 31.

To further increase the surface area of the curly wires 20 that is available for contact with thrombi, the surfaces of the curly wires 20 may be textured or may have a rough coating. Additionally or alternatively, the curly wires 20 may be provided with a drug eluting coating, for example a thrombolytic agent to facilitate pushing of the curly wires 20 into the thrombus, or a sticky coating to help retain thrombi during retraction.

Although the embodiment illustrated in FIGS. 1 to 9 has the holes 20 disposed in a line parallel to the long axis of the flexible delivery tube 18, the holes 20 may be otherwise disposed. For example, FIG. 13 shows an end view of the retrieval section of an alternative embodiment in which the curly wires 20 are offset from one another by 120 degrees—in such an embodiment, the distal ends of the curly wires 20 could be all in the same radial plane, or could be set apart from one another along the longitudinal axis of the retrieval section. Preferably, the holes 22 are positioned in the range 10 to 15 mm from the distal tip of the retrieval section 12.

FIG. 14 shows an end view of the retrieval section 12 of another alternative embodiment in which the curly wires 20 are configured so that, when in the deployed configuration, they loop about the flexible delivery tube 18 so as to have a circular shape. When the retrieval section 12 of this embodiment is positioned in a blood vessel 30 adjacent to a thrombus 32 (as shown in FIG. 15) and the curly wires 20 are deployed, they loop around the flexible delivery tube 18 and ensnare the thrombus 32 irrespective of the orientation of the holes 22. Accordingly, this embodiment obviates any need to rotationally orient the flexible delivery tube 18 prior to deployment.

Although in use the retrieval sections 12 of the embodiments of FIGS. 1 to 9 and 14 and 15 are preferably advanced so that they lie to one side of the thrombus 32 prior to deployment of the curly wires 20, as another possibility, the retrieval sections 12 may be advanced so that they are radially surrounded by the thrombus 32 prior to deployment of the curly wires 20. For the embodiment of FIG. 13, the retrieval section 12 is preferably advanced so that it is radially surrounded by the thrombus 32 prior to deployment of the curly wires 20; however, as another possibility the retrieval section 12 may be advanced so that it lies to one side of the thrombus 32 prior to deployment of the curly wires 20.

Although the above described embodiment employs thrombus engaging elements that are curly wires having semi circular or circular shapes in the transverse plane, other shapes not limited to the transverse plane could instead be employed, for example a distal-proximal oriented corkscrew shape or a pig's tail shape. The curly wires 20 should have sufficient rigidity to be able to retain their shape when the retrieval section 12 is retracted along with a thrombus.

Curly wires 20 are preferably made of a material that exhibits shape memory such as NiTi or CuZnAl that has been treated to have the desired shape (for example to have a semi-circular shape at their distal ends). As another possibility, the curly wires 40 may be made of an elastic non-memory material such as surgical grade steel.

Retrieval section 12 may further comprise one or more 'clot catching' threads, fibres or materials (not shown)

attached to its distal end to provide clotting points for any debris that is created during thrombus removal.

Retrieval section 12 may further comprise positioning means for ensuring that, prior to being brought alongside the thrombus, the flexible delivery tube 18 is located against the vessel wall and that the holes 22 are correctly oriented. Such positioning means (not shown) may comprise, for example, a balloon element positioned on one side of the flexible delivery tube 18 to push the flexible delivery tube 18 to the vessel wall. As another possibility, the positioning means may comprise an additional hole (not shown) in the flexible delivery tube 18 and an additional curly wire (not shown) that could be deployed just prior to the flexible delivery tube 18 being brought alongside the thrombus so as to push the flexible delivery tube 18 against the vessel wall. In such an embodiment, the additional curly wire could be deployable by the pushing member 23 which could push the additional curly wire out of the additional hole from the retracted configuration to an inbetween 'positioning' configuration. The flexible delivery tube 18 would then be pushed up against the vessel wall and could be advanced to the thrombus before the pushing member 23 is further advanced to its deployed configuration.

The flexible delivery tube 18 or the outer tube 24 of the pushing section 14 may comprise one or more markers than can be seen by the imaging system used to guide it to the location of the thrombus. For example, when X-ray guidance is used, the flexible delivery tube 18 may comprise one or more radiopaque bands. The markers may be positioned or shaped so as to allow an operator to determine the orientation of the holes 22 of the flexible delivery tube 18 from the imaging system. If the holes 22 themselves are observable by the imaging system, their shape and/or position may be used to orient the holes 22. As another possibility, the curly wires 22 themselves may comprise radiopaque materials to enable, when in the undeployed configuration, the orientation of the holes 22 to be determined.

Instead of the flexible catheter 10 being positioned by first positioning the delivery and removal section 16 before positioning the pushing and retrieval sections 14, 12, the pushing and retrieval sections 14, 12 may be positioned prior to the delivery and removal section 16. Although the above embodiments have been described without reference to wire guides, in a preferred embodiment the flexible delivery tube 18 has an internal lumen (not shown) for a wire guide; in use a wire guide is positioned adjacent to the thrombus before the flexible catheter 10 is delivered thereover.

A person skilled in the art will appreciate that any of the above alternatives may be employed either alone or in combination.

What is claimed is:

1. A device for the retrieval of a thrombus from a blood vessel, the device comprising:
    a delivery tube with a plurality of side holes oriented radially, the delivery tube being insertable into a blood vessel containing a thrombus; and
    one or more thrombus engaging elements for each side hole, each thrombus engaging element comprising a wire and being movable radially of the delivery tube between a retracted configuration in which it is retained within the delivery tube and a deployed configuration in which it projects from the delivery tube through the side hole, wherein each wire has a free end being movable radially of the delivery tube between the retracted and deployed configurations and is configured for piercing a thrombus, wherein a portion of each wire has a semicircular shape in a radial plane of the delivery tube after deployment and extends from the side hole to the free end in the same circumferential direction as each other one of the thrombus engaging elements.

2. The device of claim 1, wherein the free end is movable along a curved path in said radial plane between the retracted and deployed configurations.

3. The device of claim 1, wherein each thrombus engaging element is arranged so that movement of its proximal end along the delivery tube causes its distal end to move radially.

4. The device of claim 1, wherein a portion of the wire has a circular shape after deployment.

5. The device of claim 1, wherein one or more of the one or more thrombus engaging elements are made of a memory material.

6. The device of claim 5, wherein one or more of the one or more thrombus engaging elements are made of NiTi.

7. The device of claim 1, further comprising one or more radiopaque markers arranged to allow determination of the position of the plurality of side holes.

8. The device of claim 1, wherein at least a portion of one or more of the one or more thrombus engaging elements is textured.

9. The device of claim 1, wherein at least a portion of one or more of the one or more thrombus engaging elements has a cross sectional profile comprising one or more flat edges.

10. The device of claim 1, further comprising two or more thrombus engaging elements and two or more side holes, the side holes being arranged in a line parallel to a longitudinal axis of the device.

11. A device for the retrieval of a thrombus from a blood vessel, the device comprising:
    a delivery tube with at least two side holes oriented radially, the delivery tube being insertable into a blood vessel containing a thrombus; and
    one or more thrombus engaging elements for each side hole, each thrombus engaging element comprising a wire configured to pierce a thrombus and being movable radially of the delivery tube between a retracted configuration in which it is retained within the delivery tube and a deployed configuration in which it projects from the delivery tube through the side hole, wherein each thrombus engaging element is configured to curl in a radial plane of the delivery tube after deployment through the side hole, wherein all of the thrombus engaging elements curl in a clockwise direction or all of the thrombus engaging elements curl in a counterclockwise direction.

12. The device of claim 11, further comprising a pushing member for transmitting a pushing force to the one or more thrombus engaging elements, wherein the cross-sectional area of the pushing member is greater than that of the one or more thrombus engaging elements, the pushing member having a stop surface cooperating with a complementary stop surface in the delivery tube, the stop surfaces defining the deployed configuration of the one or more thrombus engaging elements by abutting each other.

13. A device for the retrieval of a thrombus from a blood vessel, the device comprising:
    a delivery tube with at least two side holes oriented radially, the delivery tube being insertable into a blood vessel containing a thrombus; and
    one or more thrombus engaging elements for each side hole, each thrombus engaging element being movable radially of the delivery tube between a retracted configuration in which it is retained within the delivery tube and a deployed configuration configured for piercing thrombi with a free end, in which it projects in a radial plane and extends from the delivery tube through the side hole to the free end in the same circumferential direction as each other one of the thrombus engaging elements, the device further comprising a positioning apparatus configured in use operable to push the delivery tube against a wall of the vessel, wherein the delivery tube further comprises a positioning hole and the positioning apparatus comprises a deployable positioning wire movable between a retracted configuration in which it is retained in the delivery tube and a positioning configuration in which it projects from the delivery tube through the positioning hole so as to push the delivery tube against a wall of the vessel.

14. The device of claim 13, wherein the deployable positioning wire is configured to curl after deployment through the positioning hole.

15. A device for the retrieval of a thrombus from a blood vessel, the device comprising:
   a delivery tube with a plurality of side holes oriented radially, the delivery tube being insertable into a blood vessel containing a thrombus; and
   one or more thrombus engaging elements for each side hole, each thrombus engaging element being movable radially of the delivery tube between a retracted configuration in which it is retained within the delivery tube and a deployed configuration in which it projects with a free end from the delivery tube through the side hole and curls in a radial plane from the side hole to the free end in the same circumferential direction as each other one of the thrombus engaging elements, wherein the one or more thrombus engaging elements have cross-sections with one or more flat sides arranged so that, when the device is in the deployed configuration and is being retracted from the vessel in a direction transverse to a direction in which each thrombus engaging element projects, contact between the one or more flat sides and a wall of the vessel acts to push the contacted thrombus engaging element away from the vessel wall.

16. A device for the retrieval of a thrombus from a blood vessel, the device comprising:
   a delivery tube with at least two side holes oriented radially, the delivery tube being insertable into a blood vessel containing a thrombus; and
   one or more thrombus engaging elements for each side hole, each thrombus engaging element comprising a wire with a free distal end and being movable radially of the delivery tube between a retracted configuration in which it is retained within the delivery tube and a deployed configuration in which the free distal end projects from the delivery tube through the side hole, wherein the one or more thrombus engaging elements are curled with a curvature that, during movement into the deployed configuration, causes the free distal end to enter into the one or more holes in the delivery tube, leaving only intermediate portions of the one or more thrombus engaging elements project from the one or more side holes wherein all of the thrombus engaging elements curl in a clockwise direction or all of the thrombus engaging elements curl in a counterclockwise direction from the side holes to the free distal ends.

* * * * *